(12) United States Patent
Jones et al.

(10) Patent No.: US 7,591,833 B2
(45) Date of Patent: Sep. 22, 2009

(54) LASER-BASED VASCULAR OCCLUSION DEVICE DETACHMENT SYSTEM

(75) Inventors: Donald K. Jones, Lauderhill, FL (US); Vladimir Mitelberg, Aventura, FL (US)

(73) Assignee: Codman & Shurtleff, Inc., Raynham, MA (US)

( * ) Notice: Subject to any disclaimer, the term of this patent is extended or adjusted under 35 U.S.C. 154(b) by 84 days.

(21) Appl. No.: 11/171,898

(22) Filed: Jun. 30, 2005

(65) Prior Publication Data
US 2007/0005100 A1  Jan. 4, 2007

(51) Int. Cl.
*A61M 29/00* (2006.01)
(52) U.S. Cl. .................................................. 606/200
(58) Field of Classification Search ............... 623/1.11, 623/1.23; 606/108, 200, 191; 604/113
See application file for complete search history.

(56) References Cited

U.S. PATENT DOCUMENTS

| | | | |
|---|---|---|---|
| 4,346,712 A | 8/1982 | Handa et al. | |
| 4,402,319 A | 9/1983 | Handa et al. | |
| 5,108,407 A | 4/1992 | Geremia et al. | |
| 5,846,247 A * | 12/1998 | Unsworth et al. | 606/108 |
| 5,989,242 A * | 11/1999 | Saadat et al. | 606/1 |
| 6,168,615 B1 | 1/2001 | Ken et al. | |
| 6,221,066 B1 * | 4/2001 | Ferrera et al. | 606/1 |
| 6,296,622 B1 | 10/2001 | Kurz et al. | |
| 6,478,773 B1 * | 11/2002 | Gandhi et al. | 604/113 |
| 6,544,225 B1 | 4/2003 | Lulo et al. | |
| 6,551,305 B2 | 4/2003 | Ferrera et al. | |
| 2005/0043755 A1 | 2/2005 | Wilson et al. | |

OTHER PUBLICATIONS

European Search Report, EP 0625324.6, Nov. 17, 2006, pp. 1-10.
European Search Report, EP 0625324.6, Feb. 21, 2008, pp. 1-4.

* cited by examiner

*Primary Examiner*—(Jackie) Tan-Uyen T Ho
*Assistant Examiner*—Melissa Ryckman
(74) *Attorney, Agent, or Firm*—Cook Alex Ltd.

(57) ABSTRACT

A vascular occlusion device deployment system for placing an occlusion device at a preselected site within the vasculature of a patient. The deployment system employing light energy transferred through an optical fiber to sever a securing filament attaching the occlusion device to the deployment system, thereby releasing the occlusion device at the preselected location.

21 Claims, 2 Drawing Sheets

LASER-BASED VASCULAR OCCLUSION DEVICE DETACHMENT SYSTEM

FIELD OF THE INVENTION

The present invention is related to deployment systems and methods for accurately deploying vascular occlusion devices at a preselected site within the vasculature of a patient, and more particularly, deployment systems that provide rapid release of vascular occlusion devices by using light transmitted through an optical fiber to break a severable securing filament connecting the occlusion device to the deployment system.

BACKGROUND OF INVENTION

The use of catheter delivery systems for positioning and deploying therapeutic devices, such as dilatation balloons, stents and embolic coils, in the vasculature of the human body has become a standard procedure for treating endovascular diseases. It has been found that such devices are particularly useful in treating areas where traditional operational procedures are impossible or pose a great risk to the patient, for example in the treatment of aneurysms in cranial blood vessels. Due to the delicate tissue surrounding cranial blood vessels, especially for example brain tissue, it is very difficult and often risky to perform surgical procedures to treat such a defect. Advancements in catheter deployment systems have provided an alternative treatment in such cases. Some of the advantages of catheter delivery systems are that they provide methods for treating blood vessels by an approach that has been found to reduce the risk of trauma to the surrounding tissue, and they also allow for treatment of blood vessels that in the past would have been considered inoperable.

Typically, these procedures involve inserting the distal end of a delivery catheter into the vasculature of a patient and guiding it through the vasculature to a predetermined delivery site. A vascular occlusion device, such as an embolic coil, is attached to the end of a delivery member which pushes the coil through the catheter and out of the distal end of the catheter into the delivery site. Some of the problems that have been associated with these procedures relate to the accuracy of coil placement. For example, the force of the coil exiting the delivery catheter may cause the coil to over shoot the predetermined site or dislodge previously deployed coils. Also, once the coil is pushed out of the distal end of the catheter, the coil cannot be retracted and may migrate to an undesired location. Often, retrieving and repositioning the coil requires a separate procedure and has the potential to expose the patient to additional risk.

In response to the above mentioned concerns, numerous devices and release mechanisms have been developed in an attempt to provide a deployment system which allows control of the occlusion device after the device has exited the catheter and provides a rapid release or detachment mechanism to release the device once it is in place. One such device is disclosed in Geremia et al. U.S. Pat. No. 5,108,407, which shows a fiber optic cable including a connector device mounted to the end to the optical fiber. An embolic coil is attached to the connector device by a heat releasable adhesive. Laser light is transmitted through the fiber optic cable to increase the temperature of the connector device, which melts the adhesive and releases the embolic coil. One drawback to using this type of system is the potential risk of melted adhesives contaminating the blood stream.

Another coil deployment system employs a pusher member having an embolic coil attached to the pusher member by a connector fiber which is capable of being broken by heat, as disclosed in Gandhi et al. U.S. Pat. No. 6,478,773. The pusher member of this arrangement includes an electrical resistance heating coil through which the connector fiber is passed. Electrical current is supplied to the heating coil by a power source connected to the heating coil via wires extending through an internal lumen of the pusher. The power source is activated to increase the temperature of the heating coil which breaks the connector fiber. One drawback is that connecting the resistance heating coil to the power source requires running multiple wires through the pusher member. Additionally, the electrical current traveling through the wires may create stray electromagnetic fields that interfere with other surgical and monitoring equipment.

Yet another embolic coil positioning and delivery system is described in Saadat et al. U.S. Pat. No. 5,989,242, which discloses a catheter having a shape memory alloy connector attached to the distal end of the catheter. The connector includes a socket having a pair of spaced-apart fingers which are responsive to a change in temperature. The fingers are bent towards each other and hold a ball which is connected to an end of an embolic coil. The connector absorbs laser light transmitted through an optical cable and transmits the light into heat energy. The heat energy raises the temperature of the connector and opens the fingers, thereby releasing the embolic coil. This type of ball and socket connection is rigid and causes the catheter to be stiff, making it difficult to guide the catheter through the vasculature of the body. This patent, and all other patents and references identified are hereby incorporated herein by reference.

Therefore, a need remains for a rapid release vascular occlusion device deployment system that is simple to manufacture, flexible and easy to guide through the vasculature of the body, minimizes the risk of foreign materials entering the bloodstream, provides enhanced and superior control over the occlusion device, and reduces the possibility of interference with other surgical and monitoring equipment.

SUMMARY OF INVENTION

The present invention is related to a deployment system and method for accurately and rapidly deploying a vascular occlusion device at a preselected site within the vasculature of a patient. The deployment system may employ an elongated flexible catheter for guiding a deployment unit to the preselected site. The deployment unit includes a delivery tube or pusher that pushes and guides the vascular occlusion device, such as an embolic coil, through the catheter to the preselected deployment site. The delivery tube includes an optical fiber, which may extend through a lumen of the delivery tube, for transmitting light energy from the proximal end of the delivery tube to the distal end of the delivery tube. The light energy preferably is provided by a laser light source operatively connected to the proximal end of the optical fiber. An element which increases in temperature upon exposure to light is located at the distal end of the delivery tube. The occlusion device is connected to the distal end of the delivery tube by a securing filament which is capable of being severed by heat. The element and the securing filament are positioned within the delivery unit so that generated heat energy causes the securing filament to break, deploying the occlusion device at the predetermined site.

It is accordingly a general aspect or object of the present invention to provide a deployment system and method for accurately deploying a vascular occlusion device within the vasculature of the body.

Another aspect or object of the present invention is to provide a deployment system and method for rapidly deploying an occlusion device.

Another aspect or object of the present invention is to provide an occlusion device deployment system and method that eliminates or minimizes risk of undesirable materials entering the body of the patient.

Another aspect or object of the present invention is to provide a deployment system in which control is retained over the occlusion device after it has exited the catheter.

Another aspect or object of the present invention is to provide a deployment system which eliminates or minimizes any interference, including electrical or magnetic interference with other equipment used in medical procedures, including surgical and monitoring equipment.

Other aspects, objects and advantages of the present invention will be understood from the following description according to the preferred embodiments of the present invention, specifically including stated and unstated combinations of the various features which are described herein, relevant information concerning which is shown in the accompanying drawings.

BRIEF DESCRIPTION OF THE DRAWINGS

In describing the preferred embodiments of the present invention, reference will be made to the accompanying drawings, wherein.

DESCRIPTION OF THE PREFERRED EMBODIMENTS

While detailed embodiments of the present invention are disclosed herein, it is to be understood that the disclosed embodiments are merely exemplary of the invention, which may be embodied in various further forms. Therefore, specific details disclosed herein are not to be interpreted as limiting, but merely as a basis for the claims and as a representative basis for teaching one skilled in the art to variously employ the present invention in any appropriate manner.

Figure 1:
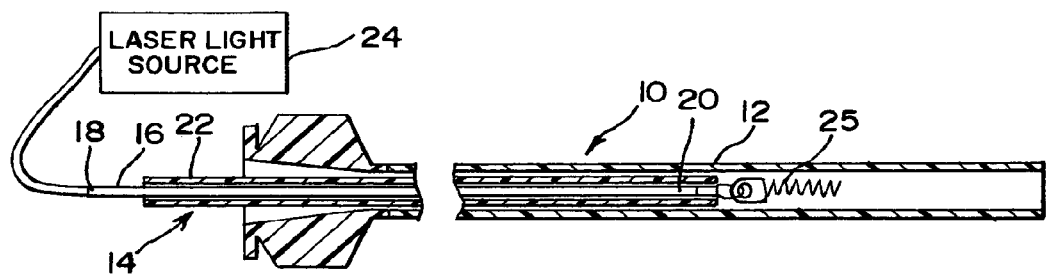
FIG. 1 is an enlarged, partially sectioned view of the vascular occlusion coil deployment system of a preferred embodiment of the present invention.

FIG. 1 generally illustrates a preferred embodiment of the vascular occlusion device deployment system of the present invention. The deployment system, generally designated at 10, includes an elongated flexible guiding catheter 12 which is inserted into the vasculature of a patient and used to guide a deployment unit 14 to a preselected site in a manner generally known in the art. The deployment unit, generally designated at 14, includes an elongated flexible optical fiber 16 which is capable of transmitting light energy from a proximal end portion 18 to a distal end portion 20. The optical fiber 16 may be comprised of any suitable material, such as quartz. The optical fiber 16 may also be housed within a delivery tube 22 which may comprise any suitable insulated or noninsulated material. A laser light source 24, for providing laser light energy, is operatively connected to the proximal end portion 18 of the optical fiber, and a vascular occlusion device, such as embolic coil 25, is connected to the distal end of the deployment unit in a manner consistent with the discussion herein.

Figure 2:
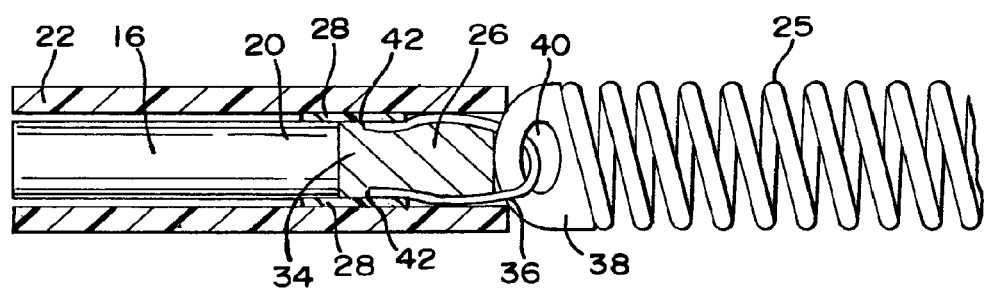
FIG. 2 is an enlarged partially sectioned view showing the deployment unit of FIG. 1 prior to placement within a catheter.
Figure 3:
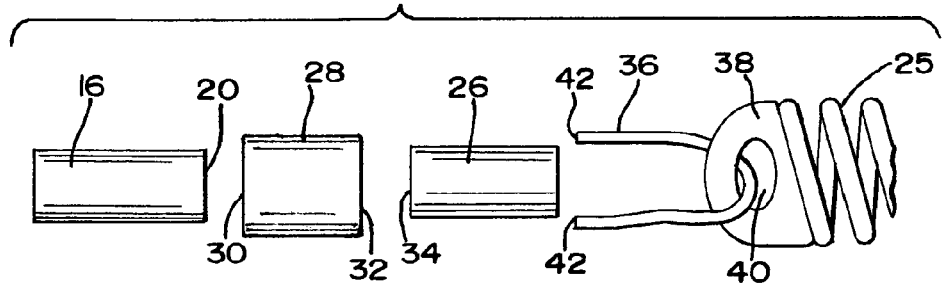
FIG. 3. is an enlarged exploded view of the distal end portion of the deployment unit.

The distal end portion of the pusher includes an element which facilitates application of energy to sever a connecting member holding the occlusion device to the deployment unit. This element is illustrated in FIGS. 2 and 3 as an element 26 connected to the distal end portion 20 of optical fiber 16. The element 26, which may be considered a heating element, is capable of absorbing light energy and converting it into heat energy. Preferably, the element 26 is a heating element comprised of any suitable metal, such as brass, brass alloy or nickel-titanium alloy. The element 26 may be attached to the distal end portion 20 of the optical fiber 16 by a shrink tubing 28 as illustrated. Preferably, the shrink tubing 28 is a heat shrink tubing which may be comprised of a polyethylene terephthalute (PET) or any other suitable material.

The illustrated arrangement of shrink tubing 28 includes a proximal end portion 30 and a distal end portion 32. The proximal end portion 30 of the shrink tubing 28 overlaps the distal end portion 20 of the optical fiber and the distal end portion 32 of the shrink tubing 28 overlaps the proximal end portion 34 of the element 26. The shrink tubing 28 is shrunk to operatively connect the element 26 to the optical fiber 16 in a secure manner. In this illustrated embodiment, the element 26 remains within the delivery tube 22 to minimize any possible contact between the element 26 and tissue of the patient.

The embolic coil 25 is connected to the delivery unit 14 by a severable securing filament 36 which is capable of being broken by energy generated at the element 26, typically by heat energy. The securing filament 36 is preferably comprised of a polymer such as a polyolefin, such as polyethylene or a polyamide such as nylon or a polyester such as PET and may be about 0.001 to 0.030 inches (about 0.025 mm to about 0.76 mm) thick, preferably, between about 0.003 and 0.015 inches (about 0.076 mm to about 0.38 mm) thick. When the filament is generally circular in cross-section, this thickness is a diameter. The securing filament 36 is designed to break when a portion of the filament is exposed to a temperature which is above body temperature. As an example, the temperature of the element 26 can, preferably, be raised to between about 45° C. and about 65° C. A higher temperature range from about 65° C. to 80° C. may be used for a very short period of time.

The embolic coil 25 may take various forms and configurations and may also be filled with a fibrous material or may be coated with a beneficial substance, such as a biogel to promote clotting. Alternatively, the embolic coil may take the form of any other occlusive device or approach known in the art such as hydrogels, foams, bioactive coils, braids, cables and hybrid devices having a suitable configuration for attachment. The illustrated embolic coin 25 is provided with a head piece 38 having an orifice 40 therethrough. The securing filament 36 loops through the orifice 40, and the ends 42 of the securing filament 36 are secured in place. In the embodiment of FIG. 2, the ends 42 are positioned to engage the shrink tubing 28; for example, ends 42 may be placed between the shrink tubing 28 and the element 26. When the shrink tubing 28 is shrunk, the ends 42 will be securely retained between the shrink tubing and the element 26, even after severance of the filament to release the vascular occlusion device.

Figure 4:
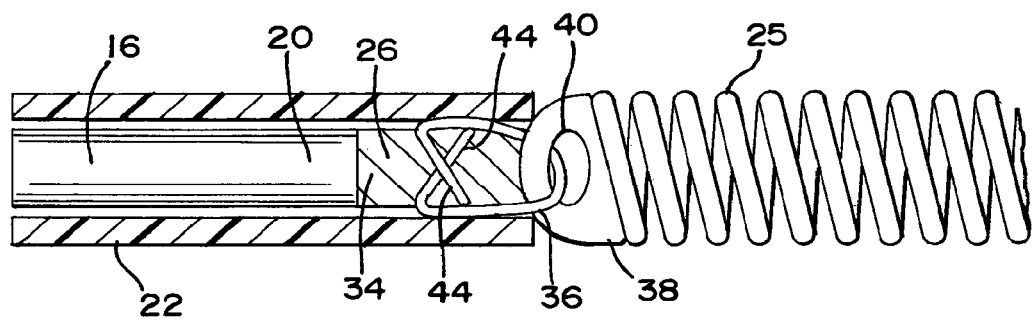
FIG. 4 is an enlarged partially sectioned view of another preferred embodiment of the deployment unit of the present invention.

In a second preferred embodiment, as illustrated in FIG. 4, the proximal end portion 34 of the element 26 may by attached to the distal end portion 20 of the optical fiber 16 by means other than shrink tubing, for example by an adhesive, such as a cyanoacrylate adhesive. Further, the securing filament 36 may be connected to the element 26 by wrapping the end lengths 44 of the securing filament around the element 26. If desired, an adhesive may be applied to the wrapped portions or end lengths 44 of the securing filament 36 for extra support.

In operation, the catheter 12 is inserted into the vasculature of the patient and positioned at a preselected location, typically in conjunction with other devices and professional procedures as generally known in the art. The delivery unit 14 is inserted into catheter 12 and once a desired location is reached, the unit 14 is advanced and/or the catheter is moved in a retrograde manner until the embolic coil 25 or other vascular occlusion device moves through the catheter and out of the distal end of the catheter. During the procedure, and before the filament has been broken, if it is determined that the distal end of the catheter 12 or the embolic coil 25 is not at the correct location, the coil 25 may be retrieved back into the distal end of the catheter so that the catheter and/or the coil may be repositioned.

Figure 5:
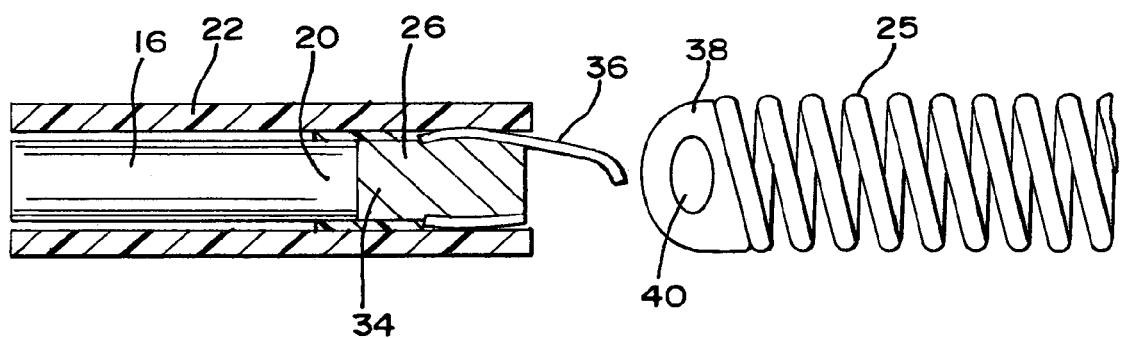
FIG. 5 is an enlarged partially sectioned view of the deployment unit showing the release of the vascular occlusion device.

When the embolic coil 25 is at the correct location and in the correct position, the laser light source 24 is activated to expose the proximal end portion 18 of the optical fiber 16 to laser light energy. The optical fiber 16 transmits the laser light energy to the distal end portion 20 of the optical fiber, exposing the element 26 to the laser light energy. The element 26 receives the laser light energy for severing the filament. In a typical approach, the element 26 absorbs the laser light energy and converts this optical energy to thermal energy, whereby the temperature of the element 26 increases. With this, the element 26 produces the necessary heat energy to sever the heat severable securing element 36, releasing the embolic coil 25 at the preselected site, as illustrated in FIG. 5.

In order to ensure that the securing filament 36 severs at only a single location, the filament may have a thickness or diameter that is smaller at the desired breakpoint location than that of the rest of the securing filament. Alternatively, the filament may be insulated except at the desired breakpoint location or exhibit a greater responsiveness to heat absorption at the desired breakpoint location by composition or physical differences.

After the filament 36 has been broken and the embolic coil 25 has been released, the delivery unit 14 may be withdrawn from the catheter 12 and a new delivery unit may be inserted to deploy another coil. This procedure may by repeated until the desired number of coils has been deployed.

It will be understood that the embodiments of the present invention which have been described are illustrative of some of the applications of the principles of the present invention. Numerous modifications may be made by those skilled in the art without departing from the true spirit and scope of the invention, including those combinations of features that are individually disclosed or claimed herein.

The invention claimed is:

1. A vascular occlusion device deployment system, comprising:
 a deployment unit comprising a flexible pusher adapted for transmitting light energy therethrough, said pusher having a proximal end portion, a distal end portion and a lumen;
 said deployment unit further comprising an optical fiber within the lumen of the pusher, the optical fiber having a distal end within the pusher lumen;
 a vascular occlusion device;
 a securing filament for connecting the vascular occlusion device to the deployment unit at a location distal of the distal end portion of the pusher, said securing filament capable of being severed by heat;
 a heating element distal of the distal end of the optical fiber and within the lumen of the pusher at the distal end portion of the pusher, said heating element having an external surface, a portion of said securing filament being between the lumen of the pusher and the external surface of said heating element; and
 the entire length of said securing filament, except for a loop length thereof that extends distally of the deployment unit and that passes through the vascular occlusion device contacts the external surface of said heating element at a contact location when said vascular occlusion device is secured to said deployment unit, said heating element increasing in temperature upon exposure to light energy transferred through said optical fiber at said contact location to provide a severed securing filament, thereby releasing the vascular occlusion device from said severed securing filament.

2. The deployment system of claim 1 wherein the pusher is disposed within a delivery tube.

3. The deployment system of claim 1 wherein the vascular occlusion device comprises an embolic coil.

4. The deployment system of claim 1 wherein a laser light source is operatively connected to the proximal end portion of the optical fiber.

5. The deployment system of claim 1 wherein said heating element is connected to the distal end of the optical fiber.

6. The deployment system of claim 1 wherein the securing filament is comprised of a polymer.

7. The deployment system of claim 1 wherein the element is comprised of a metal which increases in temperature upon exposure to light energy.

8. The deployment system of claim 1 wherein the securing filament is connected to said element.

9. The deployment system of claim 1 wherein the securing filament is connected to the distal end portion of the pusher.

10. The deployment system of claim 1 wherein the vascular occlusion device includes a headpiece having an orifice therethrough, and said loop length of the securing filament passes through the orifice.

11. A device for deploying an embolic coil to a location within the vascular system of a patient, comprising:
 a flexible pusher having a proximal end portion, a distal end portion and a lumen;
 an elongated, flexible optical fiber for transmitting light energy therethrough, said optical fiber having a distal end, a proximal end portion and a distal end portion, the distal end of the optical fiber being within the lumen of the pusher;
 a heating element connected to the distal end portion of the optical fiber, said heating element having a distal end and increasing in temperature upon absorbing light energy transferred through the optical fiber;
 a securing filament adapted to secure an embolic coil to the heating element, said securing filament capable of being severed by heat produced at said heating element, said heating element having an external surface, a portion of said securing filament being between the lumen of the pusher and the external surface of said heating element; and
 the entire length of said securing filament, except for a loop length thereof that extends distally of the distal end of the heating element and that passes through the vascular occlusion device contacts the external surface of said heating element at a contact location.

12. The deployment system of claim 11 wherein the heating element is secured to the optical fiber by a shrink tube.

13. The deployment system of claim 11 wherein a laser light source is positioned at the proximal end portion of the optical fiber.

14. The deployment system of claim 11 wherein the optical fiber and the heating element are disposed within a delivery tube.

15. The deployment system of claim 11 wherein the heating element is comprised of a metal.

16. The deployment system of claim 11 wherein the securing filament is comprised of a polymer.

17. A method for deployment of a vascular occlusion device at a preselected location within the vasculature of a patient, comprising:
   providing a deployment unit, the deployment unit comprising:
      an elongated, flexible optical fiber with a proximal end portion and a distal end portion; a heating element located distally of the distal end portion of the optical fiber;
      a pusher with a proximal end portion, a distal end portion and a lumen, the optical fiber and the heating element being disposed within the lumen;
      a vascular occlusion device connected to the deployment unit with a heat severable filament, the heating element being adjacent to the securing filament so that the entire length of said securing filament except for a loop length thereof that passes through the vascular occlusion device contacts the external surface of said heating element at a contact location;
   placing the vascular occlusion device at a preselected location in the vasculature of a patient;
   transmitting light to the distal end portion of the optical fiber;
   increasing the temperature of the heating element by exposing the heating element to the transmitted light at said contact location; and
   severing the filament with heat from the heating element, thereby deploying the vascular occlusion device at the preselected location.

18. The method of claim 17 wherein said connecting provides an embolic coil as the vascular occlusion device.

19. The method of claim 17 wherein the transmitting light comprises transmitting laser light.

20. A vascular occlusion device deployment system, comprising:
   a deployment unit comprising a flexible pusher adapted for transmitting light energy therethrough, said pusher having a proximal end portion, a distal end portion and a lumen;
   said deployment unit further comprising an optical fiber within the lumen of the pusher, the optical fiber having a distal end within the pusher lumen;
   a vascular occlusion device;
   a securing filament for connecting the vascular occlusion device to the deployment unit at a location distal of the distal end portion of the pusher, said securing filament capable of being severed by heat;
   a desired breakpoint location of the securing filament, the breakpoint location exhibits a composition or physical difference with the remainder of the length of the securing filament;
   a heating element distal of the distal end of the optical fiber and within the lumen of the pusher at the distal end portion of the pusher, said heating element having an external surface, a portion of said securing filament being between the lumen of the usher and the external surface of said heating element; and
   the entire length of said securing filament, except for a loop length thereof that extends distally of the deployment unit and that passes through the vascular occlusion device, contacts the external surface of said heating element at a contact location when said vascular occlusion device is secured to said deployment unit, said heating element increasing in temperature upon exposure to light energy transferred through said optical fiber at said contact location to provide a severed securing filament, thereby releasing the vascular occlusion device from said severed securing filament.

21. The apparatus of claim 20 wherein said desired breakpoint securing filament is provided by the securing filament having a non-uniform composition along the length of the filament.

* * * * *